United States Patent [19]

Stack

[11] Patent Number: 5,221,745

[45] Date of Patent: Jun. 22, 1993

[54] PSYCHOTROPIC PIPERIDINYLMETHYL BENZODIOXANS

[75] Inventor: Gary P. Stack, Ambler, Pa.

[73] Assignee: American Home Products Corp., New York, N.Y.

[21] Appl. No.: 882,200

[22] Filed: May 13, 1992

Related U.S. Application Data

[62] Division of Ser. No. 719,886, Jun. 21, 1991, Pat. No. 518,292.

[51] Int. Cl.$^5$ .................. C07D 417/06; C07D 491/00
[52] U.S. Cl. ........................................ 546/198; 546/16;
546/17; 546/200; 546/197; 540/520
[58] Field of Search ................... 540/520; 546/16, 17,
546/198, 200, 197

[56] References Cited

U.S. PATENT DOCUMENTS

| 4,181,802 | 1/1980 | Kennis | 546/199 |
|---|---|---|---|
| 4,873,331 | 10/1989 | Childers et al. | 544/295 |
| 4,882,432 | 11/1989 | Abou-Gharbia et al. | 544/295 |
| 4,910,302 | 3/1990 | Abou-Gharbia et al. | 544/486 |
| 4,921,958 | 5/1990 | Abou-Gharbia et al. | 544/295 |

FOREIGN PATENT DOCUMENTS

| 636238 | 2/1964 | Belgium . |
| 170213 | 2/1986 | European Pat. Off. . |
| 236930 | 9/1987 | European Pat. Off. . |
| 0252005 | 1/1988 | European Pat. Off. . |
| 1812768 | 7/1969 | Fed. Rep. of Germany . |
| 3124366 | 12/1982 | Fed. Rep. of Germany . |

OTHER PUBLICATIONS

Fozard et al., Br. J. Pharmacol., 90, 273P (1987).
J. Med. Chem, 1981, 24 1320-1328, Caroon et al.

*Primary Examiner*—C. Warren Ivy
*Assistant Examiner*—Celia Chang
*Attorney, Agent, or Firm*—Richard K. Jackson

[57] ABSTRACT

The compounds

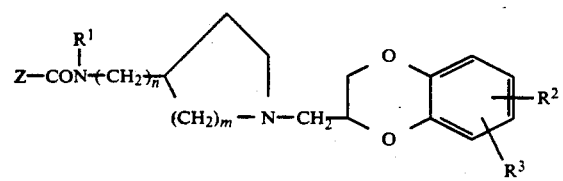

in which Z is

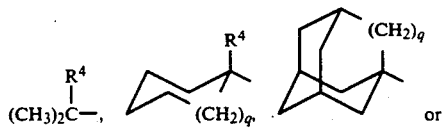

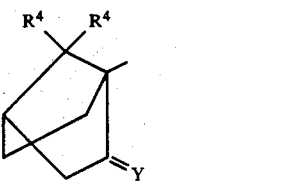

where $R^4$ is -H or alkyl; q is one of the integers 0, 1 or 2; Y is $H_2$ or O; or Z, taken with $R^1$ forms

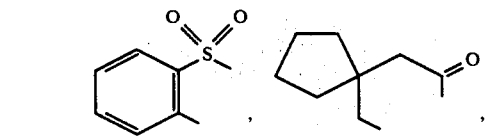

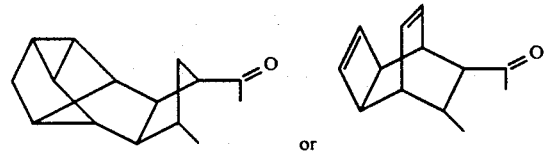

$R^1$ is hydrogen or alkyl or combined with Z as described above; $R^2$ and $R^3$ are, independently, hydrogen, alkyl, alkoxy, aralkoxy, alkanoyloxy, hydroxy, halo, amino, mono- or dialkylamino, carbamoyl or sulfonamido or $R^2$ and $R^3$, taken together are methylenedioxy, ethylenedioxy or propylenedioxy; m is one of the integers 1, 2 or 3; n is one of the integers 0 or 1; or a pharmaceutically acceptable salt thereof are antipsychotic, antidepressant and anxiolytic agents useful in relieving the symptoms of these disease states.

5 Claims, No Drawings

PSYCHOTROPIC PIPERIDINYLMETHYL BENZODIOXANS

This is a continuation division of application Ser. No. 07/719,886, filed Jun. 21, 1991, now U.S. Pat. No. 5,982,292 issued Jan. 26, 1993.

BACKGROUND OF THE INVENTION

European Patent Application EP 170,213 discloses a series of glutarimide derivatives of benzodioxan methanamine as antianxiety and antihypertensive agents. Fozard et. al. Br. J. Pharmacol. 90, 273P (1987) disclose 8-[4-(1,4-benzodioxan-2-ylmethylamino)butyl]-8-azaspiro[4.5]decane-7,9-dione (MDL 72832) as a selective and stereospecific [(−)-MDL 72832 binds 32 times as much as the dextrorotary isomer at the $5\text{-}HT_{1A}$ receptor site] ligand for $5\text{-}HT_{1A}$ receptors.

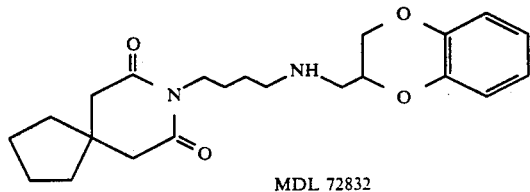

MDL 72832

European Patent EP 236,930 discloses a series of 2-substituted-alkyl-1,2-benzisothiazole-3-one 1,1-dioxide derivatives useful as anxiolytic and antihypertensive agents. Specifically claimed is 2-(4-(2,3-dihydro-1,4-benzodiox-2-yl)methylamino)butyl)-1,2-benzisothiazol-3(2H)-one 1,1-dioxide.

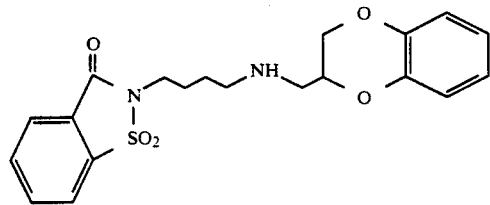

U.S. Pat. No. 4,910,302 discloses a series of psychotropic polycyclic imides as antianxiety and antipsychotic agents. Of greatest relevance to the present application are the two compounds indicated below:

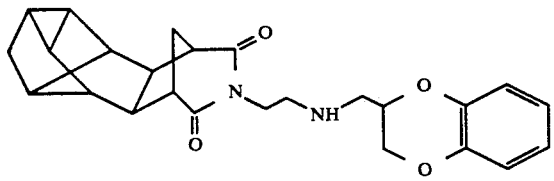

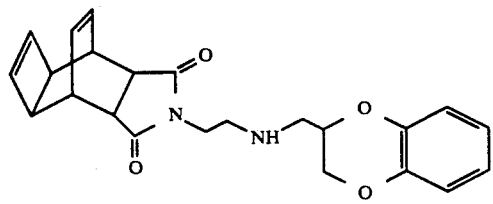

U.S. Pat. Nos. 4,921,958, 4,873,331, and 4,882,432 describe adamantyl esters, carbonates, ureas, urethans, and reverse amides as anxiolytic, antidepressant and antihypertensive agents.

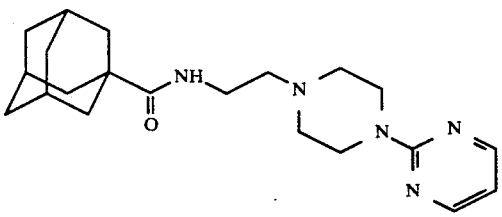

German Patent Application 1,812,768 discloses a series of 1,4-benzodioxan derivatives of structure I, in which $R^1$ is H, Cl, Me or MeO, $R^2$ is H, $C_{1-4}$ alkyl, benzyl, phenyl, or phenyl substituted by Cl, Me, MeO or $CF_3$, $A^1$ is methylene, ethylene, CO, $CH_2CO$ or $CH(OH)CH_2$, $A^2$ is methylene, ethylene or ethylidene, and Z is S, SO, or $SO_2$, as vasodilators.

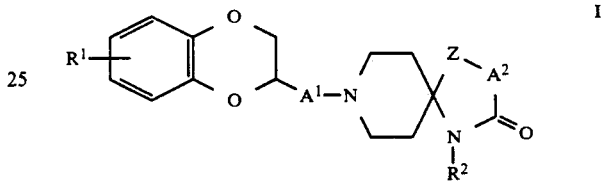

I

Belgian Patent Application Belg. 636,238 discloses a series of 1-(1,4-benzodioxan-2-yl-methyl)-4-phenyl-piperidines of formula II, wherein $R^1$ is H or F, $R^2$ is the group $(CH_2)_n NHCOR^3$, where $n=0$ or 1 and $R^3=$alkyl $(C_1\text{-}C_7)$, alkoxy $(C_1\text{-}C_7)$, cyclopropyl, benzyl, phenyl or trialkoxyphenyl, for the reduction of blood pressure.

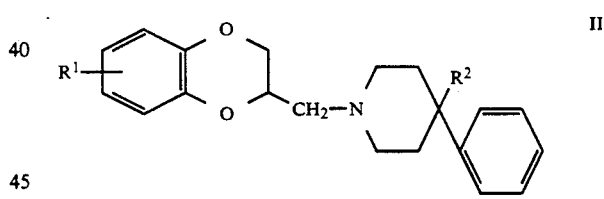

II

Ger. Offen. DE 3,124,366 discloses a series of N-oxacyclyl alkylpiperidine derivatives of structure III, in which A is (un)substituted phenylene, R, $R^1$ and $R^2$, $R^3=$H, or $C_{1-5}$ alkyl, or $R^2R^3=$A or alkylene, $R^4=$H, $C_{1-5}$ alkyl, aryl, X=O, S, NH, NMe, NBu, Y=O or S, n=1-3, p, q=1,3, p+q=4, as neuroleptics. Representative of these compounds is the agent R 4836, 1-[1-(benzo-1,4-dioxan-2ylmethyl)-4-piperidinyl]benzimidazol-2-one hydrochloride.

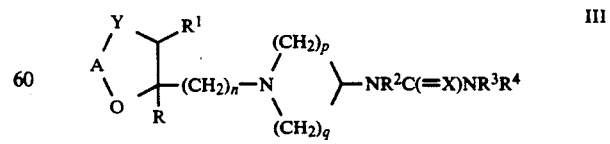

III

DESCRIPTION OF THE INVENTION

In accordance with this invention, there is provided a group of novel antipsychotic/anxiolytic agents of the formula:

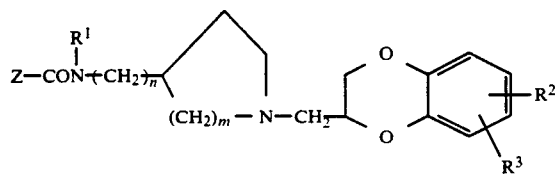

in which
Z is

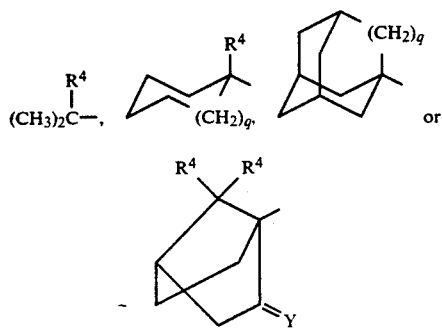

where
$R^4$ is —H or alkyl of 1 to 4 carbon atoms;
q is one of the integers 0, 1 or 2;
Y is $H_2$ or O; or
Z, taken with $R^1$ forms

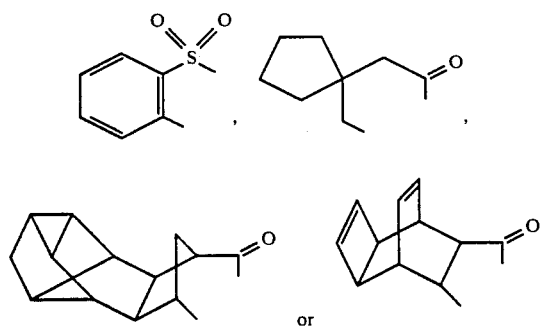

or $R^1$ is hydrogen or alkyl of 1 to 4 carbon atoms or is combined with Z as described above;

$R^2$ and $R^3$ are, independently, hydrogen, alkyl of 1 to 4 carbon atoms, alkoxy of 1 to 4 carbon atoms, aralkoxy of 7 to 12 carbon atoms, alkanoyloxy of 2 to 6 carbon atoms, hydroxy, halo, amino, mono- or dialkylamino in which each alkyl group has 1 to 4 carbon atoms, alkanamido of 2 to 6 carbon atoms or sulfonamido or $R^2$ and $R^3$, taken together are methylenedioxy, ethylenedioxy or propylenedioxy;

m is one of the integers 1, 2 or 3;
n is one of the integers 0 or 1;
or a pharmaceutically acceptable salt thereof.

Of these compounds, the preferred members are those in which Z is defined as above, $R^1$ is hydrogen or combines with Z as described above, m is the integer 2, and n, $R^2$ and $R^3$ are defined as above. Most preferred are those members in which Z is adamantyl or noradamantyl, or Z combines with $R^1$ as described above, $R^2$ and $R^3$ are hydrogen, and n is 1.

The pharmaceutically acceptable salts are those derived from such organic and inorganic acids as: acetic, lactic, citric, tartaric, succinic, maleic, malonic, hydrochloric, hydrobromic, phosphoric, nitric, sulfuric, methanesulfonic, and similarly known acceptable acids.

The compounds of this invention are prepared by conventional methods. For example, the appropriately substituted benzodioxan methanamine is combined with a suitable acid halide in the presence of an acid scavenger such as diisopropylethylamine in a solvent such as dichloromethane (1), or with a suitable anhydride, followed by a period of reflux in a high boiling solvent such as xylene, with water removal by means of a Dean-Stark trap (2). The 1,2-benzisothiazol-3(2H)-one 1,1-dioxide derivatives may be prepared by reaction of the appropriately substituted benzodioxan methanamine with methyl 2-(chlorosulfonyl)-benzoate in the presence of a tertiary amine such as diisopropylethylamine, followed by treatment of the resulting amide with a base such as dimethylaminopyridine (DMAP) in refluxing xylene (3).

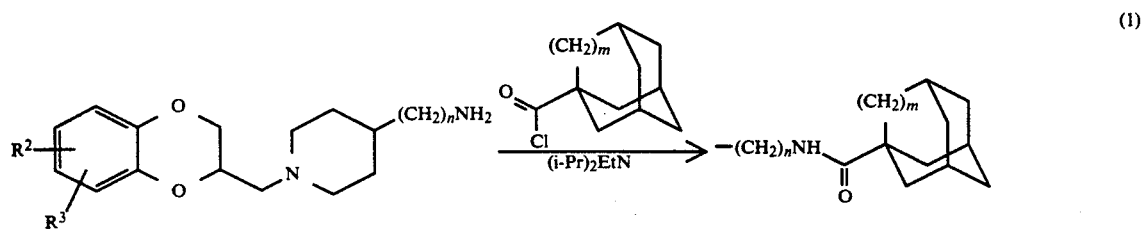

(1)

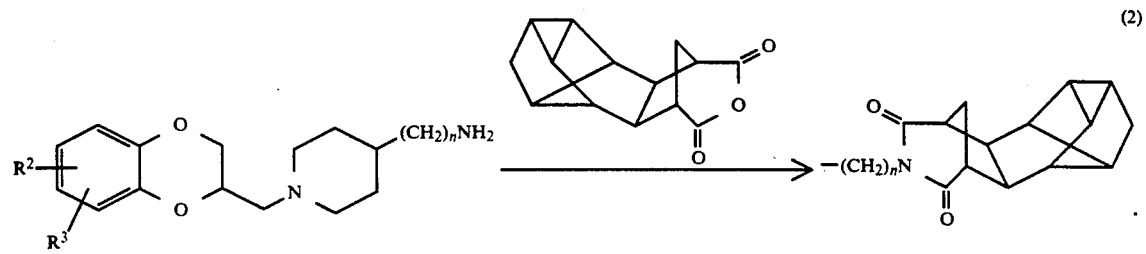

(2)

(3)

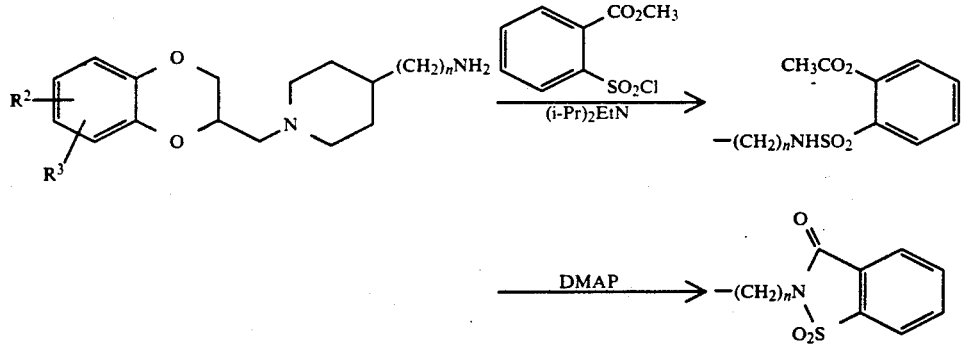

Finally, the compounds of the invention may be more generally prepared (4) by reaction of the suitably substituted cyclic amine with the appropriate benzodioxan methyl halide or tosylate in the presence of an acid scavenger such as diisopropylethylamine in a high boiling solvent such as dimethylformamide.

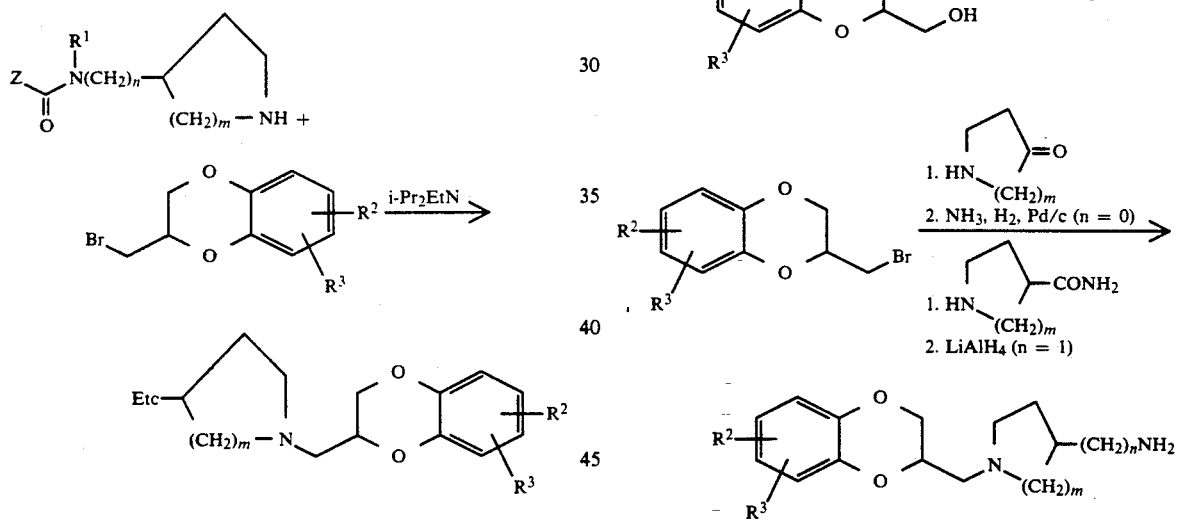

The bicyclic carboxylic acids described by Z are known compounds or they can be readily synthesized by one schooled in the art. Adamantane and noradamantane-1-carboxylic acids are commercially available; ketopinic acid can be prepared from camphorsulfonyl chloride by the method of Bartlett and Knox (Organic Synthesis, Vol 45, p. 55) and can be converted to apocamphane-1-carboxylic acid by the method described in J. Am. Chem. Soc., 61, 3184 (1939). The benzodioxan methanamines and methyl halides themselves are known compounds, or they can readily be derived from the appropriate salicylaldehyde by the procedure illustrated below:

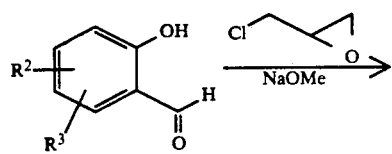

The compounds of this invention possess high affinities for the dopamine D-2 receptor and the serotonin 5-HT$_{1A}$ receptor, and consequently, they are useful as antipsychotic, antidepressant and anxiolytic agents for the treatment of a variety of central nervous system disorders such as depression, paranoia, schizophrenia, anxiety, sleep disorders, sexual dysfunction, addiction, and related problems.

High affinity for the dopamine D-2 receptor was established by the standard experimental test procedure of Fields, et al., Brain Res., 136, 578 (1977) and Yamamura et al., eds., Neurotransmitter Receptor Binding, Raven Press, N.Y. (1978) wherein homogenized limbic brain tissue is incubated with $^3$H-spiroperidol and various concentrations of test compound, filtered and washed and shaken with Hydrofluor scintillation cocktail (National Diagnostics) and counted in a Packard 460 CD scintillation counter. The results of this testing with compounds representative of this invention are given below.

High affinity for the serotonin 5-HT$_{1A}$ receptor was established by testing the claimed compound's ability to displace [$^3$H] 8-OHDPAT (dipropylaminotetralin) from the 5-HT$_{1A}$ serotonin receptor following the procedure of Hall et al., J. Neurochem. 44, 1685 (1985). This procedure is employed to analogize this property of the claimed compounds with that of buspirone, which is a standard for anxiolytic activity, and, like the compounds of this invention, displays potent affinity for the 5-HT$_{1A}$ serotonin receptor subtype. The anxiolytic activity of buspirone is believed to be, at least partially, due to its 5-HT$_{1A}$ receptor affinity (Vander Maclen et al., Eur. J. Pharmacol. 1986, 129 (1–2) 133–130).

The results of the two standard experimental test procedures described in the preceding two paragraphs were as follows:

| Compound | D-2 Binding (% Inhibition at 1 μM) | 5-HT$_{1A}$ Binding (% Inhibition at 0.1 μM) |
|---|---|---|
| Example 1 | 29% | 59% (IC$_{50}$ = 107 nM) |
| Example 2 | | 4% |
| Example 3 | | 45% |
| Example 4 | 97% | 96% |
| Example 5 | 52% | 92% |

Hence, the compounds of this invention demonstrated high affinity for both the serotonin 5-HT$_{1A}$ and dopamine D$_2$ receptor subtypes, and are therefore useful in the treatment of multi-CNS disorders amenable to treatment with antipsychotic, antidepressant and anxiolytic agents. As such, the compounds of this invention may be administered orally or parenterally to a mammal in need of antipsychotic, antidepressant and/or anxiolytic medical treatment in an amount sufficient to alleviate the symptoms of the disease state.

Applicable solid carriers for the compounds of this invention can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis or state of anxiety or depression and the size, age and response pattern of the patient.

The following examples illustrate the production of representative compounds of this invention.

EXAMPLE 1

N-[1-[(2,3-Dihydro-1,4-benzodioxin-2-yl)methyl]-4-piperidinyl]tricyclo[3.3.1.1$^{3,7}$]decane-1-carboxamide To an anhydrous solution of 3.0 ml (17 mmole) of diisopropylethylamine and 1.2 g (4.9 mmole) 1-[(2,3-dihydro-1,4-benzodioxin-2-yl)methyl]-4-aminopiperidine in 150 ml of dichloromethane maintained at 0° C. in an ice/salt water bath was added 0.99 g (5.0 mmole) of adamantane-1-carbonyl chloride in 75 ml of dichloromethane. The mixture was allowed to come to room temperature and stirred overnight. It was then washed with 300 ml each of water, saturated aqueous sodium bicarbonate, saturated sodium chloride solution, dried over magnesium sulfate, filtered and concentrated in vacuum. The crude residue was filtered through 75 g of silica gel, using 2.5% methanol in dichloromethane as eluant, and the product-containing fractions evaporated to give 2.3 g of yellow oil. This was dissolved in dichloromethane and brought to a boil. Isopropanol was slowly added to replace the boiling dichloromethane, then 5.0 ml of 4N isopropanolic HCl was added. Upon cooling, 1.67 g (75% yield) of the title compound, monohydrochloride, hemihydrate, (m.p. 246°–250° C.) precipitated as a white powder.

Elemental Analysis for: C$_{25}$H$_{34}$N$_2$O$_3$.HCl.½H$_2$O: Calcd: C, 65.84; H, 7.95; N, 6.14. Found: C, 65.75; H, 7.96; N, 6.19.

EXAMPLE 2

3a,4,4a,6a,7,7a-Hexahydro-2-[1-[(2,3-Dihydro-1,4-benzodioxin-2-yl)methyl]-4-piperidinyl]-4,7-etheno-1H-cyclobut[f]isoindole-1,3(2H)-dione 1-[(2,3-Dihydro-1,4-benzodioxin-2-yl)methyl]-4-aminopiperidine (1.0 g, 4.0 mmole) and hexahydro-4,7-etheno-1H-cyclobut[f]isobenzofuran-1,3-(2H)-dione (0.88 g, 4.3 mmole) were combined in 40 ml of xylene and the mixture was refluxed for 44 hours under nitrogen, with water removal being accomplished by means of a Dean-Stark trap. Upon cooling, the mixture was column chromatographed on 75 g of silica gel with toluene, then dichloromethane, and finally 2.5% methanol/dichloromethane as eluant. The product-containing fractions were combined and concentrated in vacuum, and the residue (1.38 g) crystallized from 50 ml of isopropanol with the addition of 10 ml of 4N isopropanolic HCl. to give 1.3 g of the title compound as a white solid, monohydrochloride, quarter hydrate, m.p. 262°–272° C.

Elemental Analysis for: $C_{26}H_{28}N_2O_4 \cdot HCl \cdot \frac{1}{4}H_2O$: Calcd: C, 65.95; H, 6.27; N, 5.91. Found: C, 65.84; H, 6.38; N, 5.84.

EXAMPLE 3

2-[1-[(2,3-Dihydro-1,4-benzodioxin-2-yl)methyl]-4-piperidinyl]-1,2-benzoisothiazol-3(2H)-one 1,1-dioxide 1-[(2,3-Dihydro-1,4-benzodioxin-2-yl)methyl]-4-aminopiperidine (1.3 g, 5.2 mmole), diisopropylethylamine (6.8 ml, 39 mmole) and methyl 2-(chlorosulfonyl)-benzoate (1.6 g, 6.8 mmole) were combined in 80 ml of dichloromethane and the mixture was stirred at room temperature under nitrogen for 3 hours. The mixture was then washed with saturated aqueous sodium bicarbonate, dried over magnesium sulfate, filtered and concentrated in vacuum. The residue was column chromatographed on 100 g of silica gel with first 30%, then 50% ethyl acetate/pet ether as eluant. The product-containing fractions were combined and concentrated in vacuum to give 1.88 g of the intermediate sulfonamide, with the expected NMR. This was redissolved in 40 ml of xylene and 0.60 g of dimethylaminopyridine added. This mixture was refluxed under nitrogen for 4 days. It was allowed to cool to room temperature and filtered through 75 g of silica gel, using 2.5% methanol/dichloromethane to completely remove the product. The product was concentrated in vacuum and the residue crystallized from isopropanol with the addition of 4N isopropanolic HCl to give 1.21 g of the title compound as a white solid, monohydrochloride, m.p. 224°–230° C.

Elemental Analysis for: $C_{21}H_{22}N_2O_5S \cdot HCl$: Calcd: C, 55.93; H, 5.14; N, 6.21. Found: C, 55.85; H, 5.06; N, 6.25.

EXAMPLE 4

3-[[1-[(2,3-Dihydro-1,4-benzodioxin-2-yl)methyl]-4-piperidinyl]methyl]decahydro-2H-1,5-methano-6,7,9-methenopentaleno[1,2-d]azepine-2,4(3H)-dione 1-[(2,3-Dihydro-1,4-benzodioxin-2-yl)methyl]-4-aminomethylpiperidine (1.38 g, 5.26 mmole) and decahydro-1,5-methano-6,7,9-methenopentaleno[1,2-d]oxepine-2,4(1H,5H)-dione (1.68 g, 7.3 mmole) were combined in 100 ml of xylene and the mixture was refluxed for 48 hours under nitrogen, with water removal being accomplished by means of a Dean-Stark trap. Upon cooling, the mixture was concentrated in vacuum and the residue column chromatographed on 50 g of silica gel with 1.5% methanol/dichloromethane as eluant. The product-containing fractions were combined and concentrated in vacuum, and the residue crystallized from isopropanol with the addition of 4N isopropanolic HCl to give 0.53 g of the title compound as a white solid, monohydrochloride, m.p. 248°–252° C.

Elemental Analysis for: $C_{29}H_{34}N_2O_4 \cdot HCl$: Calcd: C, 68.16; H, 6.90; N, 5.48. Found: C, 67.87; H, 6.99; N, 5.35.

EXAMPLE 5

N-[[1-[(2,3-Dihydro-1,4-benzodioxin-2-yl)methyl]-4-piperidinyl]methyl]tricyclo[3.3.1.1$^{3,7}$]decane-1-carboxamide To an anhydrous solution of 9.0 ml (52 mmole) of diisopropylethylamine and 1.7 g (6.5 mmole) 1-[(2,3-dihydro-1,4-benzodioxin-2-yl)methyl]-4-aminomethylpiperidine in 125 ml of dichloromethane maintained at 0° C. in an ice/salt water bath was added dropwise over 40 minutes a solution of 1.5 g (7.8 mmole) of adamantane-1-carbonyl chloride in 50 ml of dichloromethane. The mixture was then poured onto 400 ml of ice, the ice allowed to melt and the organic phase removed in a separatory funnel. After dilution to 400 ml with additional dichloromethane, the organic phase was washed with 400 ml each of saturated aqueous sodium bicarbonate, saturated sodium chloride solution, dried over magnesium sulfate, filtered and concentrated in vacuum. The crude residue (3.6 g) was flash chromatographed on 250 g of silica gel using 2.5% methanol in dichloromethane as eluant, and the product-containing fractions evaporated to give 2.1 g of free base. This was dissolved in dichloromethane and brought to a boil. Isopropanol was slowly added to replace the boiling dichloromethane, then 6.0 ml of 2N isopropanolic HCl was added. Upon cooling, 1.88 g (47% yield) of the monohydrochloride of the title compound (m.p. 254°–256° C.) precipitated as white crystals.

Elemental Analysis for: $C_{26}H_{36}N_2O_3 \cdot HCl$: Calcd: C, 67.73; H, 8.09; N, 6.08. Found: C, 67.55; H, 8.06; N, 5.85.

What is claimed is:

1. A compound of the formula:

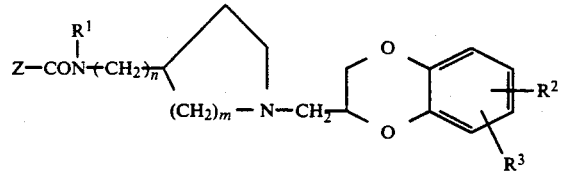

in which Z, taken with $R^1$ forms

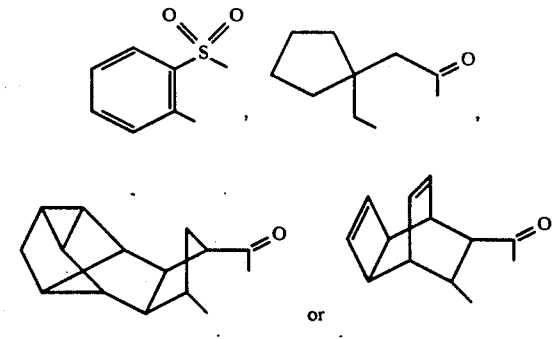

and $R^2$ and $R^3$ are, independently, hydrogen, alkyl of 1 to 4 carbon atoms, alkoxy of 1 to 4 carbon atoms, alkanoyloxy of 2 to 6 carbon atoms, hydroxy, halo, amino, mono- or dialkylamino in which each alkyl group has 1 to 4 carbon atoms, alkanamido of 2 to 6 carbon atoms or $R^2$ and $R^3$, taken together are methylenedioxy, ethylenedioxy or propylenedioxy; m is 2;

n is one of the integers 0 or 1;
or a pharmaceutically acceptable salt thereof.

2. A compound of claim 1 in which $R^2$ and $R^3$ are hydrogen and n is 1 or a pharmaceutically acceptable salt thereof.

3. A compound of claim 1 which is 3a, 4, 4a, 6a, 7, 7a-hexahydro-2-[1-[(2,3-dihydro-1,4-benzodioxin-2-yl)methyl]-4-piperidinyl]-4,7-etheno-1H-cyclobut[f]-isoindole-1,3(2H)-dione, or a pharmaceutically acceptable salt thereof.

4. A compound of claim 1 which is 2-[1-[(2,3-dihydro-1,4-benzodioxin-2-yl)methyl]-4-piperidinyl]-1,2-benzoisothiazol-3(2H)-one 1,1-dioxide, or a pharmaceutically acceptable salt thereof.

5. A compound of claim 1 which is 3-[[1-[(2,3-dihydro-1,4-benzodioxin-2-yl)methyl]-4-piperidinyl]methyl]decahydro-2H-1,5-methano-6,7,9-methenopentaleno[1,2-d]azepine-2,4(3H)-dione, or a pharmaceutically acceptable salt thereof.

* * * * *